US009471975B2

(12) United States Patent
Gessner et al.

(10) Patent No.: US 9,471,975 B2
(45) Date of Patent: Oct. 18, 2016

(54) METHODS, SYSTEMS AND COMPUTER PROGRAM PRODUCTS FOR DYNAMIC OPTICAL HISTOLOGY USING OPTICAL COHERENCE TOMOGRAPHY (71) Applicant: Bioptigen, Inc., Morrisville, NC (US)

(72) Inventors: Ryan Gessner, Carrboro, NC (US); Eric L. Buckland, Hickory, NC (US)

(73) Assignee: Bioptigen, Inc., Morrisville, NC (US)

( * ) Notice: Subject to any disclaimer, the term of this patent is extended or adjusted under 35 U.S.C. 154(b) by 50 days.

(21) Appl. No.: 14/520,837

(22) Filed: Oct. 22, 2014

(65) Prior Publication Data
US 2015/0110376 A1    Apr. 23, 2015

Related U.S. Application Data (60) Provisional application No. 61/894,182, filed on Oct. 22, 2013.

(51) Int. Cl.
G06K 9/00 (2006.01)
G06T 7/00 (2006.01)
A61B 3/10 (2006.01)

(52) U.S. Cl.
CPC ............ G06T 7/0012 (2013.01); A61B 3/102 (2013.01)

(58) Field of Classification Search
None
See application file for complete search history.

(56) References Cited

U.S. PATENT DOCUMENTS

| | | | |
|---|---|---|---|
| 7,301,644 B2 | 11/2007 | Knighton et al. | |
| 7,505,142 B2 | 3/2009 | Knighton et al. | |
| 7,554,669 B2 | 6/2009 | Buckland et al. | |
| 7,869,663 B2 | 1/2011 | Buckland et al. | |
| 8,401,257 B2 | 3/2013 | Izatt et al. | |
| 8,442,356 B2 | 5/2013 | Buckland et al. | |
| 8,644,572 B2 * | 2/2014 | Izatt ............................. | 382/128 |
| 8,687,856 B2 | 4/2014 | Bower et al. | |
| 8,744,159 B2 | 6/2014 | Bower et al. | |
| 8,787,623 B2 | 7/2014 | Bower et al. | |
| 2006/0055936 A1 * | 3/2006 | Yun ................... | G01N 21/4795 356/479 |
| 2006/0164653 A1 * | 7/2006 | Everett ................... | A61B 3/102 356/479 |
| 2007/0002327 A1 * | 1/2007 | Zhou ...................... | A61B 3/102 356/456 |
| 2007/0025642 A1 * | 2/2007 | Buckland ............... | A61B 3/102 382/294 |
| 2007/0115481 A1 | 5/2007 | Toth et al. | |
| 2007/0258094 A1 * | 11/2007 | Izatt .................... | G01B 9/02044 356/456 |
| 2007/0263227 A1 * | 11/2007 | Mujat .................... | A61B 3/102 356/511 |
| 2011/0160576 A1 | 6/2011 | Bower et al. | |
| 2012/0194783 A1 | 8/2012 | Wei et al. | |
| 2012/0275677 A1 | 11/2012 | Bower et al. | |
| 2013/0301008 A1 * | 11/2013 | Srivastava ......... | G01B 9/02083 351/246 |

OTHER PUBLICATIONS

Qi Yang, Charles A. Reisman, Zhenguo Wang, Yasufumi Fukuma, Masanori Hangai, Nagahisa Yoshimura, Atsuo Tomidokoro, Makoto Araie, Ali S. Raza, Donald C. Hood, and Kinpui Chan, "Automated layer segmentation of macular OCT images using dual-scale gradient information," Opt. Express 18, 21293-21307 (2010).*
Garvin, Mona Kathryn. "Automated 3-D segmentation and analysis of retinal optical coherence tomography images." PhD (Doctor of Philosophy) thesis, University of Iowa, 2008.<http://ir.uiowa.edu/etd/29>.*
Ishikawa H, 2005—Macular segmentation with optical coherence tomography. Ishikawa H, Stein DM, Wollstein G, Beaton SA, Fujimoto JG, Schuman JS. Inves Ophthal Vis Sci 2005; 46: 2012-7.*
Jonathan Oakley, Optical Coherence Tomography Imaging of Diseases of the Central Nervous System, http://www.voxeleron.com/optical-coherence-tomography-imaging-diseases-central-nervous-system/, Sep. 18, 2014.*

* cited by examiner

*Primary Examiner* — Andrae S Allison
(74) *Attorney, Agent, or Firm* — Myers Bigel & Sibley (57) ABSTRACT

Methods of acquiring an image are provided. The methods include deriving a first boundary surface from a volumetric image; deriving a second boundary surface, different and spaced apart from the first boundary surface, of the volumetric image, the first and second boundary surfaces defining a slice of the volumetric image therebetween; and deriving at least one intermediate thin section between the first and second boundary surfaces, the thin section having a thickness that is less than a thickness of the slice of the volumetric image defined by the first and second boundary surfaces. Systems and computer program products are also provided.

9 Claims, 9 Drawing Sheets

METHODS, SYSTEMS AND COMPUTER PROGRAM PRODUCTS FOR DYNAMIC OPTICAL HISTOLOGY USING OPTICAL COHERENCE TOMOGRAPHY

CLAIM OF PRIORITY

The present application claims priority from U.S. Provisional Application No. 61/894,182, filed Oct. 22, 2013, the disclosure of which is hereby incorporated herein by reference as if set forth in their entirety.

FIELD

The present inventive concept relates to optical coherence tomography (OCT) and, more particularly, microscopy, histology, optical tissue sectioning, confocal optical imaging, and optical coherence tomography (OCT) and related systems and computer program products.

BACKGROUND

In many applications of biological imaging and machine vision it is desirable to obtain three dimensional, volumetric images of a sample. Photographic and topologic representations of surface structure and features provide important, but limited, information about a sample. It is often desirable to visualize the interior of samples for diagnostic purposes.

There are many techniques for obtaining tomographic and volumetric images of samples. Generally a radiation source, imaging methodology, and image reconstruction methodology are chosen to match the transmissive properties and scale of the sample. For example, conventional techniques may include Magnetic resonance imaging (MRI), computed tomography (CT) scans and positron emission tomography (PET) scans.

In the optical domain, optical coherence tomography (OCT) has obtained significant traction for its ability to acquire depth resolved images with longitudinal and lateral resolutions relevant to investigation of biological tissues, and has been adopted as a standard of care in clinical retina diagnostics.

OCT has the capability to resolve structures at resolutions of better than 10 µm, with the potential to serve as a non-invasive substitute to sectioning histology. In order to be a successful substitute to histology, OCT image acquisition and processing methods must take advantage of thick-section imaging to create visualizations that highlight tissue physiopathology in longitudinal and lateral dimensions at cellular or near-cellular resolution, on living subjects.

SUMMARY

Some embodiments of the present inventive concept provide methods of acquiring an image. The methods include deriving a first boundary surface from a volumetric image; deriving a second boundary surface, different and spaced apart from the first boundary surface, of the volumetric image, the first and second boundary surfaces defining a slice of the volumetric image therebetween; and deriving at least one intermediate thin section between the first and second boundary surfaces, the thin section having a thickness that is less than a thickness of the slice of the volumetric image defined by the first and second boundary surfaces.

In further embodiments, the at least one intermediate thin section may conform to a contour of the first and/or second boundary surface.

In still further embodiments, the at least one intermediate section may be a plurality of intermediate sections. A first intermediate section of the plurality of the intermediate sections may be adjacent to the first boundary surface and may be derived. derived from data that is axially conformal with the first boundary surface. A second intermediate section of the plurality of the intermediate sections may be adjacent to the second boundary surface and may be derived from data that is axially conformal with the second boundary surface.

In some embodiments, a third intermediate section of the plurality of the intermediate sections may be positioned between the first and second intermediate sections and derived from data between the first and second intermediate sections. The third intermediate section may not be conformal to the first or the second intermediate section and may have an intermediate shape that logically transitions between the first and second intermediate sections.

In further embodiments, the slice of the volumetric image may include an en face projection derived from an entire region between the first and second boundary surfaces. The en face projection may be derived from pixels that form the entire region between the first and second boundary surfaces.

In still further embodiments, the at least one intermediate section may include an en face projection derived from a fraction of the entire region between the first and second boundary surfaces. The en face projection derived from a fraction of the entire region between the first and second boundary surfaces may be derived from a subset of the pixels that form the entire region between the first and second boundary surfaces.

In some embodiments, the volumetric image may be acquired using optical coherence tomography (OCT), for example, Fourier domain OCT (FDOCT).

In further embodiments, the at least one thin section may be displayed.

DETAILED DESCRIPTION

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Although many of the examples discussed herein refer to the sample being an eye and specific elements of an eye including the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As discussed above, OCT has the capability to resolve structures at resolutions of better than 10 µm, with the potential to serve as a non-invasive substitute to sectioning histology. In order to be a successful substitute to histology, OCT image acquisition and processing methods must take advantage of thick-section imaging to create visualizations that highlight tissue physiopathology in longitudinal. As illustrated in FIG. 2A, conventional en face image may include artifacts that make the image fuzzy or unclear. In accordance with embodiments discussed herein, improved en face images with reduced presence of artifacts may be provided as illustrated in FIG. 2B. Details with respect to various embodiments of the present inventive concept will be discussed below with respect to FIGS. 1 through 8.

Figure 1:
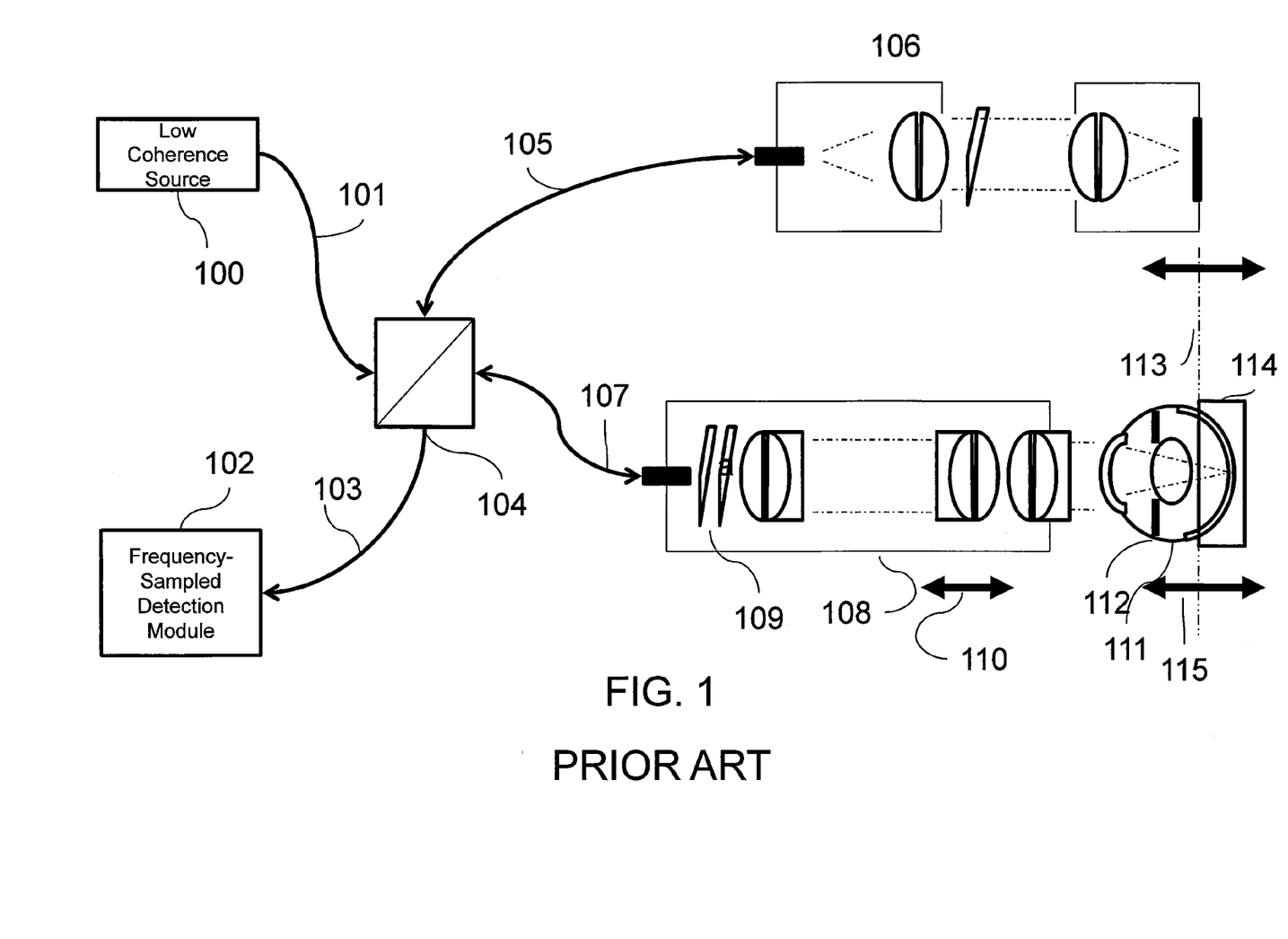
FIG. 1 is a diagram illustrating a conventional ophthalmic Fourier domain optical coherence tomography (FDOCT) system.
Figure 2A:
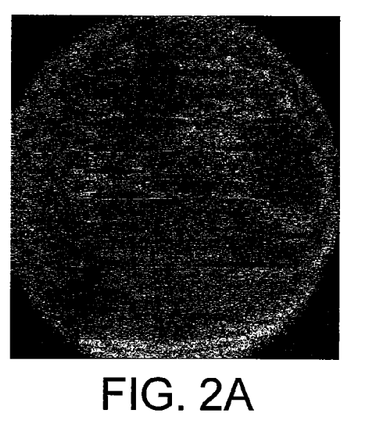
FIG. 2A is an en face image derived from a planar section drawn from a volumetric optical coherence tomography data set illustrating artifacts associated with a lack of conformance between the planar section and the shape of a sample.
Figure 2B:
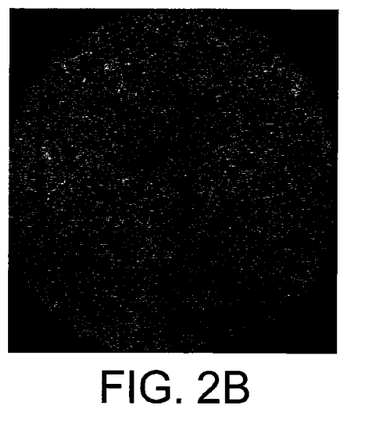
FIG. 2B is an en face image produced in accordance with embodiments of the present inventive concept.

Referring first to FIG. 1, a Fourier domain optical coherence tomography (FDOCT) system in accordance with some embodiments of the present inventive concept will be discussed. Although embodiments of the present inventive concept are illustrated herein as using a Fourier domain optical coherence tomography (FDOCT) system to acquire a three dimensional depth-resolved image of the sample, embodiments of the present inventive concept are not limited to this configuration. Any one of a variety of implementations of optical coherence tomography or confocal optical microscopy may be used to acquire a three dimensional depth-resolved image of the sample without departing from the scope of the present inventive concept.

As illustrated in FIG. 1, the system includes a broadband optical source 100 directed along a source path 101 to a beamsplitter 104 where the source radiation is divided into a reference path 105 and a sample path 107. The reference light is returned through a reference reflection device 106 back through the beamsplitter 104, where it mixes with the light returned from a sample, such as the retina of an eye 111. The resultant wavelength dependent interferogram is directed through a detection path 103 to a detection module 102. The total spectral interferogram is processed using Fourier transforms to derive a spatial domain depth resolved image.

In contrast to a time domain OCT system, where the reference mirror scans a range over time that matches the depth range of interest for image the subject to acquire a temporal interferogram, the FDOCT system acquires a spectral interferogram from a fixed reference position 113 that is path length matched to a target axial position with respect to the subject. The spectral interferogram contains information for all depths within a window 114. The window is defined by parameters of detection as is known in the art. A scanning subsystem 108 includes a pair of scanning galvo mirrors 109 and an objective lens set with focal capabilities 110. For posterior, or retinal, ophthalmic imaging, the scanned OCT beam is directed through the pupil of the eye 112 to image the retina. An FDOCT system may include a serial acquisition of spectral information using a broadband swept frequency optical source, or a parallel acquisition of spectral information using a broadband low coherence source and a spectrometer, or a combination of these methods. A spectrometer based system is referred to as spectral domain optical coherence tomography (SDOCT) and a swept source system is referred to swept source OCT (SSOCT).

Operations of the system of FIG. 1 in accordance with some embodiments of the present inventive concept will be discussed. The FDOCT system may acquire a three dimensional image in accordance with embodiments discussed herein. The broadband source 100 of electromagnetic radiation, such as a superluminescent diode, a swept laser, or a supercontinuum laser, is coupled to the system through a source path 101. The source 101 is split at an optical splitter 104 to deliver a portion of the radiation to a reference path 105 and a portion of the radiation to the sample path 107. The sample, for example an eye, is illuminated through delivery optics that couple the sample path to the sample as illustrated. Light at least partially transmitting into the sample is backscattered, collected by collection optics that, in some embodiments, may be the same as the delivery optics. This backscattered sample light is mixed with radiation that has traversed the reference path to create a spectral interferogram. The spectral interferogram is detected by a photodetector configured to detect elements of the optical radiation across a spectrum of the source, with the various detected elements having a central wavelength, equivalently optical frequency or wavenumber, and an associated optical bandwidth. The array of detected spectral elements of the spectral interferogram is processed from the frequency domain to the spatial domain using an inverse Fourier transform.

The spatial image that is derived by this process is an "A-scan" that possesses depth resolved structural information along a propagation direction, z, of the optical radiation, at a resolution that is inversely proportional to the total detected optical bandwidth, an image depth that is inversely proportional to the frequency interval of the spectral domain data elements and constrained by photon attenuation propagating through the sample, and a lateral resolution dependent on the focusing characteristics of the delivery optics.

In Fourier domain optical coherence tomography, a volumetric image is generally a collection of depth-resolved "A-scans" or A-lines arrayed into a plane along one lateral dimension, x, to create a "B-scan", and a collection of B-scans or B-slices offset along a direction, y, to create a volumetric image. If the spacing of A-scans is constant along the x and y directions, the image may be termed "isotropically sampled." A truly isotropic image will have equal spacing in all directions x, y, and z, but this is not generally the case in practice due to the decoupling of longitudinal and lateral resolution that is an attribute of OCT.

OCT images are most commonly viewed as cross-sectional B-scans. This view is typically orthogonal to the grain of a biological tissue, and may be very useful for measuring tissue layers, observing tissue structures, and pathophysiological structural variations in a region of a sample. This view is also orthogonal to a typical histological section, or C-slice. A histological section creates a view specific to a particular tissue layer, uncovering information about the structure, and implying information about the histochemistry and vascularity, for example, of a particular tissue type at a particular location.

It is desirable to create histological sections non-invasively using the optical techniques of confocal microscopy and OCT. Such techniques may be referred to as "sectioning optical histology." The utility of sectioning optical histology is limited by issues of resolution, artifacts of motion during image acquisition illustrated in FIG. 2A, and the lack of conformity of a tissue layer shape with a planar cut or C-scan.

Current Fourier domain OCT systems, such as the Envisu R2200 and Envisu R4100 offered by Bioptigen deliver longitudinal resolutions better that 3.0 µm and 2.0 µm, respectively. Lateral resolution is a function of optical design, and lateral resolution of better than 2.0 µm is achieved in the imaging of the retina of mice. At this resolution, relevant cellular and subcellular structural detail is observed.

When imaging a living subject, such as in investigations of the retina using mouse models, subject respiration and shifting body positions create periodic and aperiodic disturbances that present challenges in image re-creation and subsequent sectioning by image processing. These artifacts of motion illustrated, for example, in FIG. 2A, may be corrected in accordance with some embodiments of the present inventive concept as illustrated, for example, in FIG. 2B.

In particular, tissue layers are not rigid planes, but have shape that may vary from one layer to another. The presence of pathology may further perturb the shape of tissue layers. A planar cut along a volumetric image, no matter where constructed, will not in general extract a plane conformal to a tissue layer. The resulting en face image derived from a planar cut will have artifacts as observed in FIG. 2A.

In order to derive an optical section consistent with the needs of a histological evaluation of tissue, it is desirable to acquire an image sampled at least nominally isotropically along the (x,y) dimension orthogonal to the depth, or z-axis, formed by the optical propagation direction. In some embodiments of the present inventive concept, a "raster scan" is acquired with A-scans acquired on centers separated by no more than an equivalent lateral optical resolution of the imaging system in both x, and y directions. More sparsely acquired data may suffice, at the risk of gaps in the acquired data set.

Figure 3A:
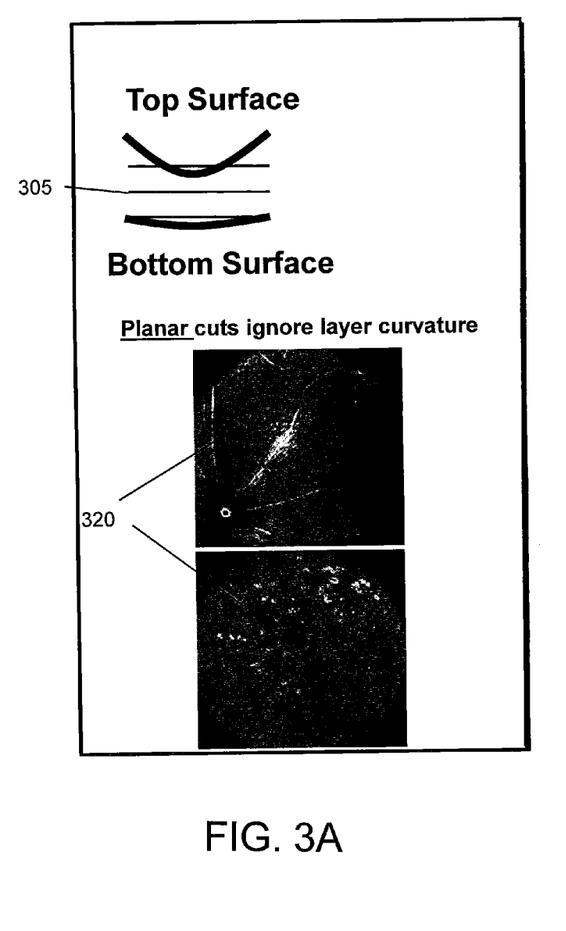
FIGS. 3A through 3C are diagrams and images illustrating optical sectioning in accordance with some embodiments of the present inventive concept.
Figure 3B:
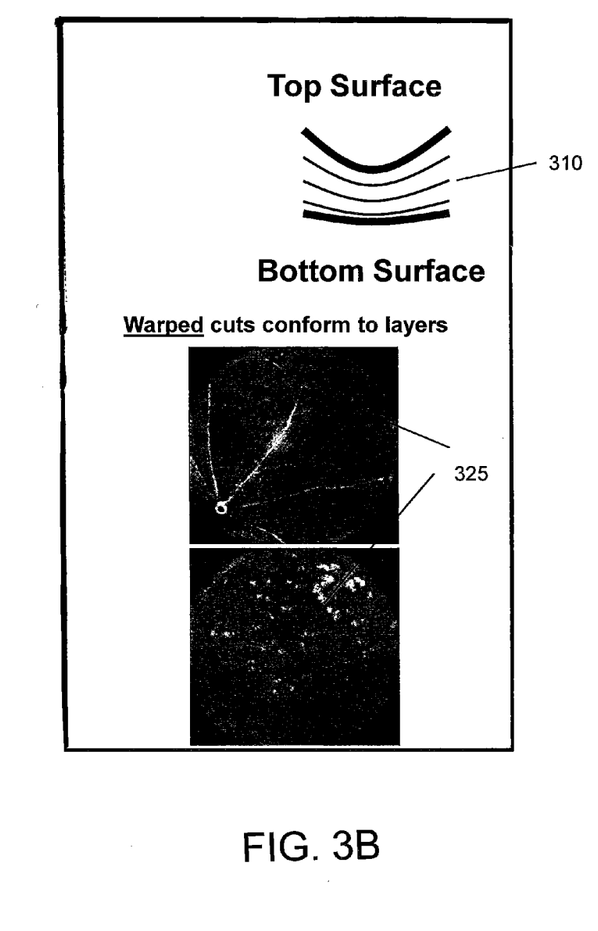

FIGS. 3A and 3B diagrams illustrating thick and thin slices in accordance with embodiments of the present inventive concept will be discussed. As illustrated in FIGS. 3A and 3B, an image of a thick optical section is defined between a top surface and a bottom surface of a sample. As used herein, a "thick optical section" is an image of a sample acquired with a depth-scanning confocal microscope or an OCT system (Thick Section Type I), or segmented images within the primary sample (Thick Section Type II). A Thick Section Type II refers to a region, generally, multiple pixels thick derived from boundary layers within the full sample that are either identified in an automated manner, a manual manner, or a combination of the two. As further used herein, a "thin optical section" refers to an en face projection derived from a fraction of the thick section, i.e. between a top surface and bottom surface of the thick optical section. Layers 305 in FIG. 3A and layers 310 in FIG. 3B illustrate thick optical sections in accordance with some embodiments of the present inventive concept. Thus, in accordance with some present inventive concept thin optical sections may be derived between a pair of boundary surfaces in a volumetric optical image.

As illustrated in FIG. 3A, the thick optical section is defined by a top and bottom surface and the thin optical sections 305 are in between. However, in FIG. 3A, the planar cuts or thin optical sections ignore the curvature of the top and bottom surfaces. In stark contrast, the thin optical sections 310 of FIG. 3B are warped to conform to the curvature of the top and bottom surfaces of FIG. 3B, which, as illustrated by the scans of FIGS. 3A (320) and 3B (325) provide improved en face images (325).

Figure 3C:
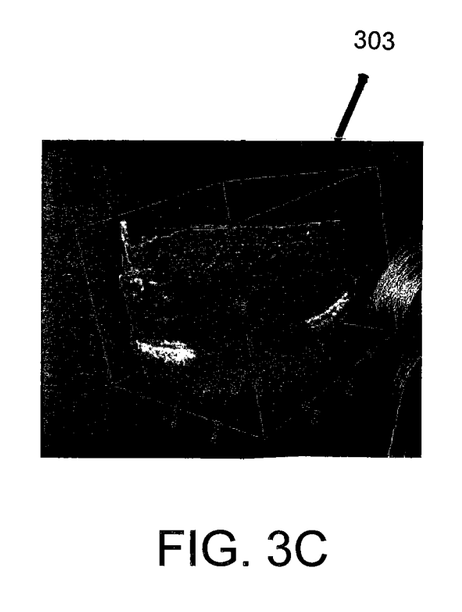

Referring to FIGS. 3A and 3B, in some embodiments of the present inventive concept, an optical sectioning procedure begins by acquiring a volumetric optical image 303 illustrated in FIG. 3C. A first boundary surface (bottom surface of FIGS. 3A and 3B) is identified using any one of available image segmentation techniques. An en face image, or C-slice, is derived from, and conformal to, the first boundary surface (320, 325). In these embodiments, the boundary surface may be the boundary between any distinct structural layers in a sample or any other boundary surface deemed useful. The conformal en face image may be a projection that is precisely one image-pixel in thickness or multiple pixels in thickness without departing from the scope of the present inventive concept. The en face projection may be specific (x,y,z) pixel values, may be interpolations between pixel values at two neighboring pixels in x, y, or z, may be sums or averages of a range of pixels, may be a weighted sum or weighted average of a range of pixels, or may be a value determined by a histogram of pixel values. The precise manner of computing the en face pixel value may thus be selected to meet any particular visualization objective.

As further illustrated in FIGS. 3A and 3B, a second boundary surface (top surfaces of FIGS. 3A and 3B) is identified, the second surface is different than the first surface, thus, defining a thickness or "thick optical section." The second surface may contact the first at one or points, but in general, to be useful, will not cut through or across the first surface, though this constraint is not absolute and reflects more on physiological utility than the procedure itself.

Generally, as illustrated, the second boundary surface may not, and need not, be conformal to the first boundary surface. As further illustrated in FIGS. 3A and 3B, an en face image (320, 325) of the second boundary surface is derived. The specific pixel value assignment logic used for the second boundary surface may the same as that chosen for the first boundary layer, or may be different to reflect a specific visualization objective for the second boundary layer without departing from the scope of the present inventive concept.

Accordingly, an en face sectioned image derived from the first surface and the second surface as, for example, a projection that may be a summed, averaged, weighted averaged, histogram, or otherwise computed projection of the pixel values between the first boundary surface and the second boundary surface, may be provided. Thus, this en face sectioned image may represent information conformal to the first surface and conformal to the second surface.

As discussed above, the image of a sample acquired with a depth-scanning confocal microscope or an OCT system may be considered a "thick optical section." An en face image derived between two segmented boundary layers may also be considered a thick optical section.

Generally, there is significant important pathophysiology variation within a thick section, and a technique to explore the variation across the thick section is highly desirable. For example, vascularity that resides within such a thick section is not generally uniformly distributed, nor are pathologies such as edemas, schesis, or tumors. Therefore, a technique to extend thick section to thin section optical histology is very important according to some embodiments of the present inventive concept.

Therefore, as discussed above, "thin optical sections" may be derived between any pair (top and bottom surfaces as illustrated in FIGS. 3A and 3B, of boundary surfaces in a volumetric optical image. As discussed above with respect to FIG. 3B, thin optical sections may be derived specifically in a manner that dynamically conforms the thin section from shape of the first boundary surface to the shape of the second boundary surface in a systematic and deterministic manner.

Figure 4:
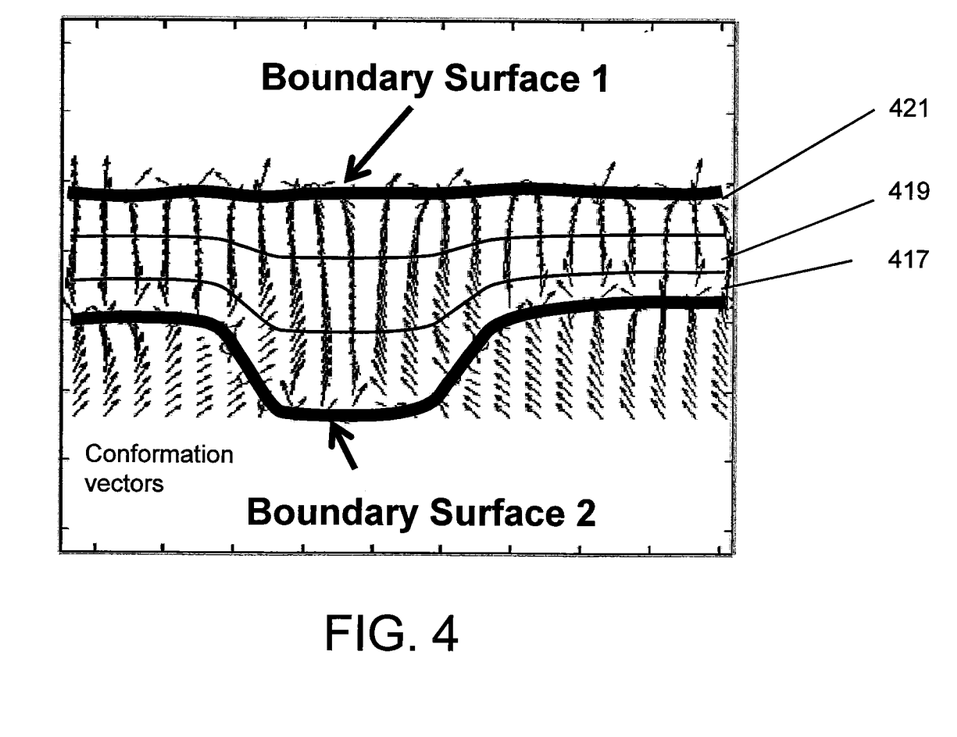
FIG. 4 is a diagram illustrating dynamically conforming a section from a first surface having one shape to a second surface having a second shape in accordance with some embodiments of the present inventive concept.

Referring now to FIG. 4, details of acquiring thick and thin optical sections in accordance with some embodiments of the present inventive concept will be discussed. As illustrated in FIG. 4, a first and a second boundary surface are derived from a volumetric optical image as described above. As used herein, a thick optical section refers to an en face projection derived from the entire region between the first and second boundary surfaces. As further used herein, a thin optical section refers to an en face projection derived from a fraction of the thick section. A thin section en face projection or C-slice, is derived from a subset of pixels that form the thick optical section. For clarity, a thin section may be defined, as relative to a thick section, according to various properties of interest. A thin section may be a fraction of the volume of a corresponding thick section, where the fraction may be one-half or less. A thin section may be defined by a number of image pixels along the z-direction. A thin section may be derived from a number of pixels that is one-half or less the number of pixels of a corresponding thick section. A thin section may defined in terms of a multiple of the axial (depth direction) optical resolution of the optical system. A thin section thickness may be less than or equal to an axial resolution of the optical system, or may be greater than an optical resolution in thickness but less than the thickness of the corresponding thick section. There may be circumstances where the thick section, defined by two boundary surfaces, is a thickness of only one or two pixels or one or two optical resolutions. In these embodiments, there may be no distinguishing practical difference between the thick section and the thin section.

As further illustrated in FIG. 4, one or more thin section en face projections 417, 419 and 421 are derived from within the volumetric data set that contains a thick section (between surfaces 1 and 2) as defined above. In other words, there is an identified first boundary surface and an identified second boundary surface, and it is at least possible to derive a thick section en face projection from the pixel values between the first and second boundary surfaces. In some embodiments, a sequence of one or more thin optical sections 417, 419 and 421 is derived between the limits of the first and the second boundary surface. Although three thin sections are illustrated in FIG. 4 between the first and second boundaries, embodiments of the present inventive concept are not limited by this configuration. For example, less than or more than three thin sections may be derived without departing from the scope of the present inventive concept.

In particular, in some embodiments, a sequence of two or more thin sections are derived, such that a first thin section 421 is coincident with or in the immediate vicinity of the first boundary surface, and this first thin 421 section is derived from data that is axially conformal with this first boundary section. A second thin section 417 is coincident with or in the immediate vicinity of the second boundary surface, and this second thin section 417 is derived from data that is axially conformal with this second boundary section.

In still further embodiments, a sequence of three or more thin sections are derived, such that a first thin section 421 is registered to or in the immediate vicinity of the first boundary surface, and this first thin section 421 is derived from data that is axially conformal with this first boundary section. A second thin section 417 is registered to or in the immediate vicinity of the second boundary surface, and this second thin section 417 is derived from data that is axially conformal with this second boundary section. At least a third thin section 419 is derived at least in part from data that is between the first and second thin sections 421/417, and warped such that this third thin section 419 is conformal neither perfectly to the first thin section or the second thin section, but rather to an intermediate shape function that is a logical transition from the first boundary surface to the second boundary surface. In these embodiments, there may be a plurality of thin sections, such that the thin section in closest proximity to the first boundary surface shares conformal similarity to that boundary surface and the thin section closest to the second boundary surface, and intermediate thin sections share a degree of conformal similarity to each surface in relation to that sections proximity to each surface.

Figure 5:
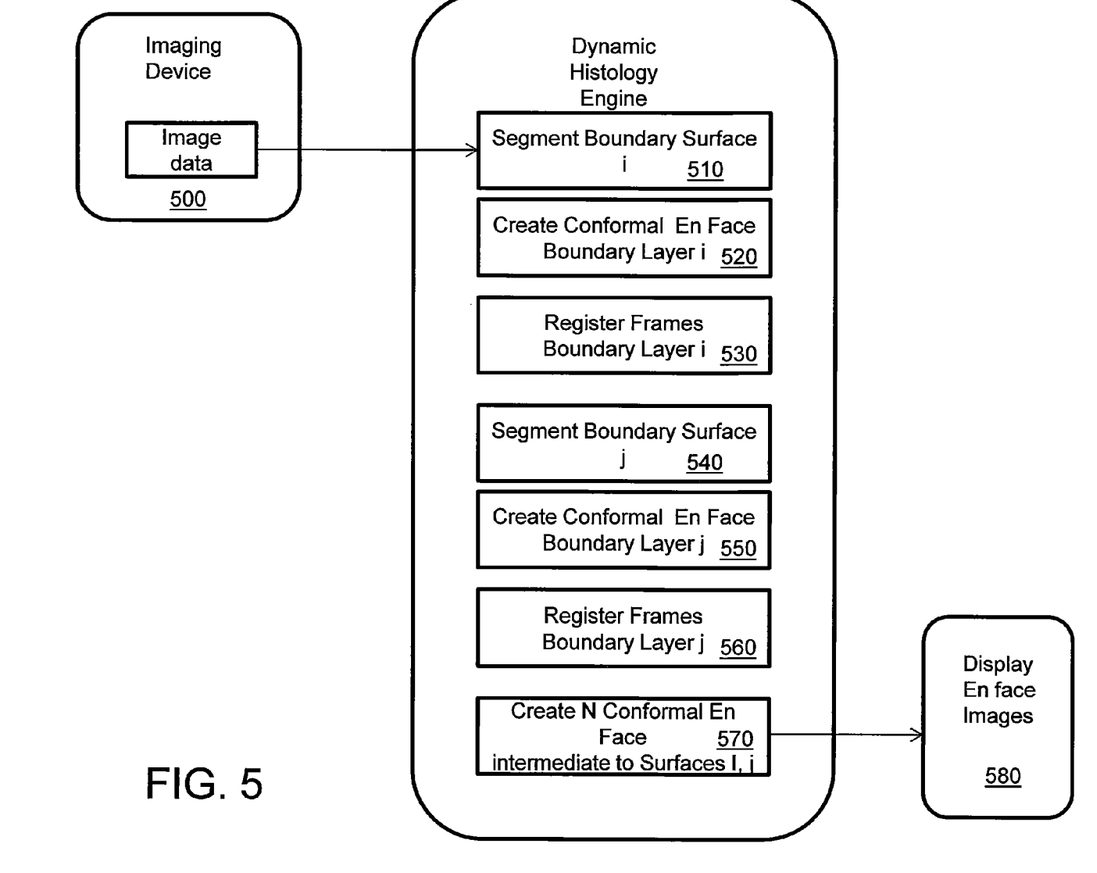
FIG. 5 is a flow chart illustrating operations for obtaining conformal thin optical sections from a thick optical data set in accordance with some embodiments of the present inventive concept.

Referring now to FIG. 5, operations for deriving thin sections in accordance with embodiments of the present inventive concept discussed above will be discussed. Operations begin at block 500 by deriving a thick section having first and second boundary surfaces as discussed above with respect to FIG. 4. Operations continue by determining a number N of thin sections to be derived from the thick section. In other words, how may thin sections will the thick section be divided into where a first thin section is centered on the first boundary surface and a last thin section is centered on the second boundary surface.

The first boundary surface (i) of the thick section may be segmented (block 510) and a conformal en face boundary layer i may be created (block 520). The frames may then be registered to boundary layer i (block 530). Operations of blocks 510-530 may be repeated in blocks 540-560 for the second boundary layer j. Then, N (decided above) conformal en face intermediate thin slices may be created (block 570).

In some embodiments, at each surface position (x,y) the distance z between the first boundary surface and second boundary step is divided into (N−1) equidistant steps. An internal surface (x_i, y_i, z_i) may be derived for each axial step between the first and second boundary surfaces. A thickness may be set for each internal en face projection image, where the thickness may be either in absolute or fractional values relative to the number of thin sections (N) into which the thick section is divided. An en face image derived from pixel values within the thickness set for the thin section may be computed (block 570). These en face images may be derived using any of the available summation, averaging, weighted average, histogram or other desired function without departing from the scope of the present inventive concept. Any one or more of the thin sections may be displayed (block 580).

In some embodiments where the intermediate value $z_i$ does not precisely correspond to a data pixel, a value may be obtained by, for example, choosing a nearest neighbor or through any other interpolation function.

As discussed above, the data set may represent optical intensities derived directly from the OCT or confocal images for each positional value $(x_i, y_i, z_i)$. However, this is not necessary with respect to all embodiments. The initial image intensity values may be processed in any way to create a secondary image to meet the objectives of the visualization. For example, the data contrast and brightness scales may be adjusted; may be mapped to a color code; may be binned into a histogram; may represent statistical properties of the data; may represent texture values of the data; or may be manipulated in any way known to the art for accentuating or diminishing features or interest without departing from the scope of the present inventive concept.

The data may also be represented in the spectral domain that is the Fourier transform of the spatial data, and this spectral data may also be processed into a representation set that meets specific visualization objectives. As long as there is a three dimensional data set that may be represented as values that can be processed into an image, the methods of the present inventive concept may be applicable.

The boundary surfaces and internal surfaces discussed herein have not been expressly registered, aligned, or otherwise manipulated to remove gaps and artifacts of motion. In some embodiments of the present inventive concept, any of the surfaces described may have gaps in data; these gaps may be filled with any desired method of interpolation without departing from the scope of the present inventive concept.

Figure 6:
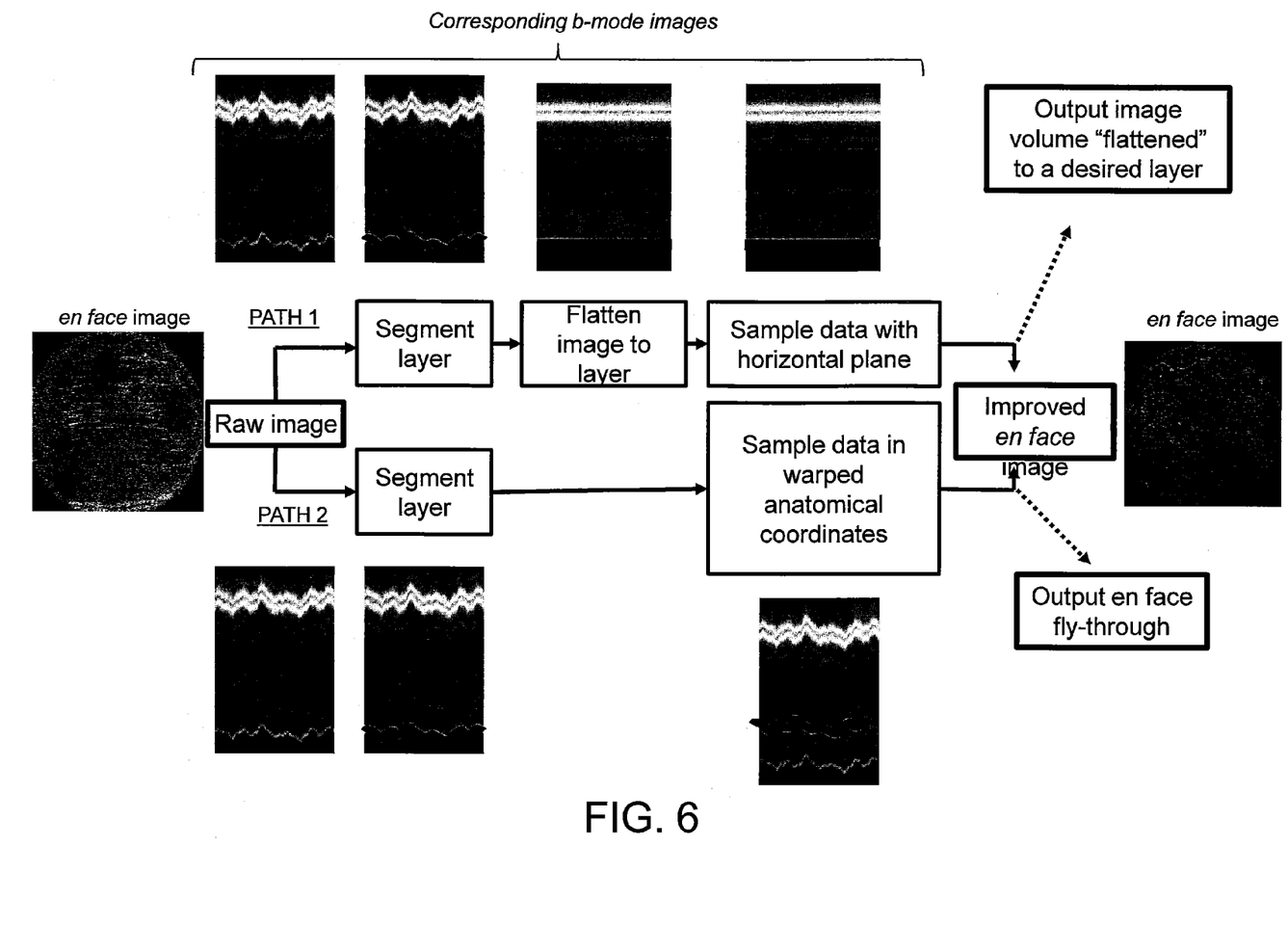
FIG. 6 is a diagram illustrating two algorithmic pathways for obtaining conformal optical sections, including one pathway that includes registering frames of an image to each other in accordance with some embodiments of the present inventive concept.

Referring now to FIG. 6, two algorithmic pathways (PATH 1 and PATH 2) for obtaining sections in accordance with embodiments of the present inventive concept will be discussed. As illustrated therein, the artifacts of motion in the slow axis of data collection (e.g. elevation direction orthogonal to a B-scan in a typical OCT raster scan) may be flattened (PATH 1) to a specific boundary layer. Each B-scan may be registered to its neighboring B-scan, for example by maximizing the cross-correlation function between B-scans. This cross-correlation may be set to operate on a cross-sectional region of data that comprises all or a portion of the image data of the sample, or may be narrowed to a stripe of data that accentuates the data in a particular boundary layer of interest, or may be further narrowed to boundary layer of interest in a particular lateral region of interest. This first stage of cross-correlation, lateral structural variation across a B-scan direction, is not flattened.

Some embodiments of the present inventive concept use a single boundary surface (i.e. segmentation) in conjunction with a second artificially generated plane or surface that may be either orthogonal to the propagation of light or otherwise oriented as the second boundary surface.

In further embodiments, the data set may be flattened in both the x and y (B-scan and elevation) direction. In this case the entire data set is registered, for example, using a cross-correlation to a narrow subset of data, constrained to a lateral region and boundary layer of interest. While this registration creates an artificial topologic view of the data, it provides an interesting relative view physiology or pathology, relative to the correlate kernel. In this way, a multiplicity of volumetric representations may be derived for choosing a correlation kernel at a different boundary layer and/or a different lateral position of interest. When a volume is reconstructed after such registration, and the sequence of B-scans viewed as movie, differential structures become particularly well accentuated. Furthermore, it becomes easier to visualize along the two orthogonal faces (x,z) or (y,z) (B-scan and elevation).

An additional benefit of this localized flattened registration, and a further embodiment of the present inventive concept, is the ability to project the data along three orthogonal views to obtain a unique composite projection, not unlike an x-ray. This set of triplet views is particularly useful to regionalize pathology and physiology in a meaningful representation without needing to scan through the volume or deal with artifacts of motion during image acquisition. In this way, in embodiments described for en face representations, thick and thin optical composites of perpendicular to the B-scan direction may be obtained. Such composite views are uniquely useful for showing clusters of pathology along the depth direction. This concept may be further extended to obtaining sectional views along any axis within the volume in accordance with some embodiments of the present inventive concept.

Some aspects of the present inventive concept may be implemented by a data processing system. Exemplary embodiments of a data processing system 730 configured in accordance with embodiments of the present inventive concept will be discussed with respect to FIG. 7. The data processing system 730 may include a user interface 744, including, for example, input device(s) such as a keyboard or keypad, a display, a speaker and/or microphone, and a memory 736 that communicate with a processor 738. The data processing system 730 may further include I/O data port(s) 746 that also communicates with the processor 738. The I/O data ports 746 can be used to transfer information between the data processing system 730 and another computer system or a network using, for example, an Internet Protocol (IP) connection. These components may be conventional components such as those used in many conventional data processing systems, which may be configured to operate as described herein.

Figure 7:
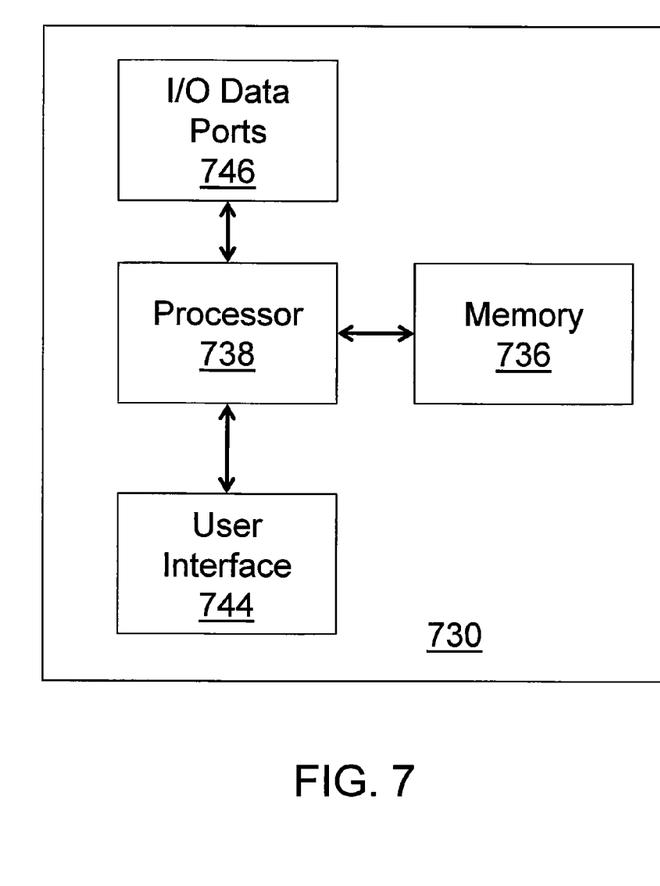
FIG. 7 is block diagram illustrating a data processing system configured in accordance with embodiments of the present inventive concept.
Figure 8:
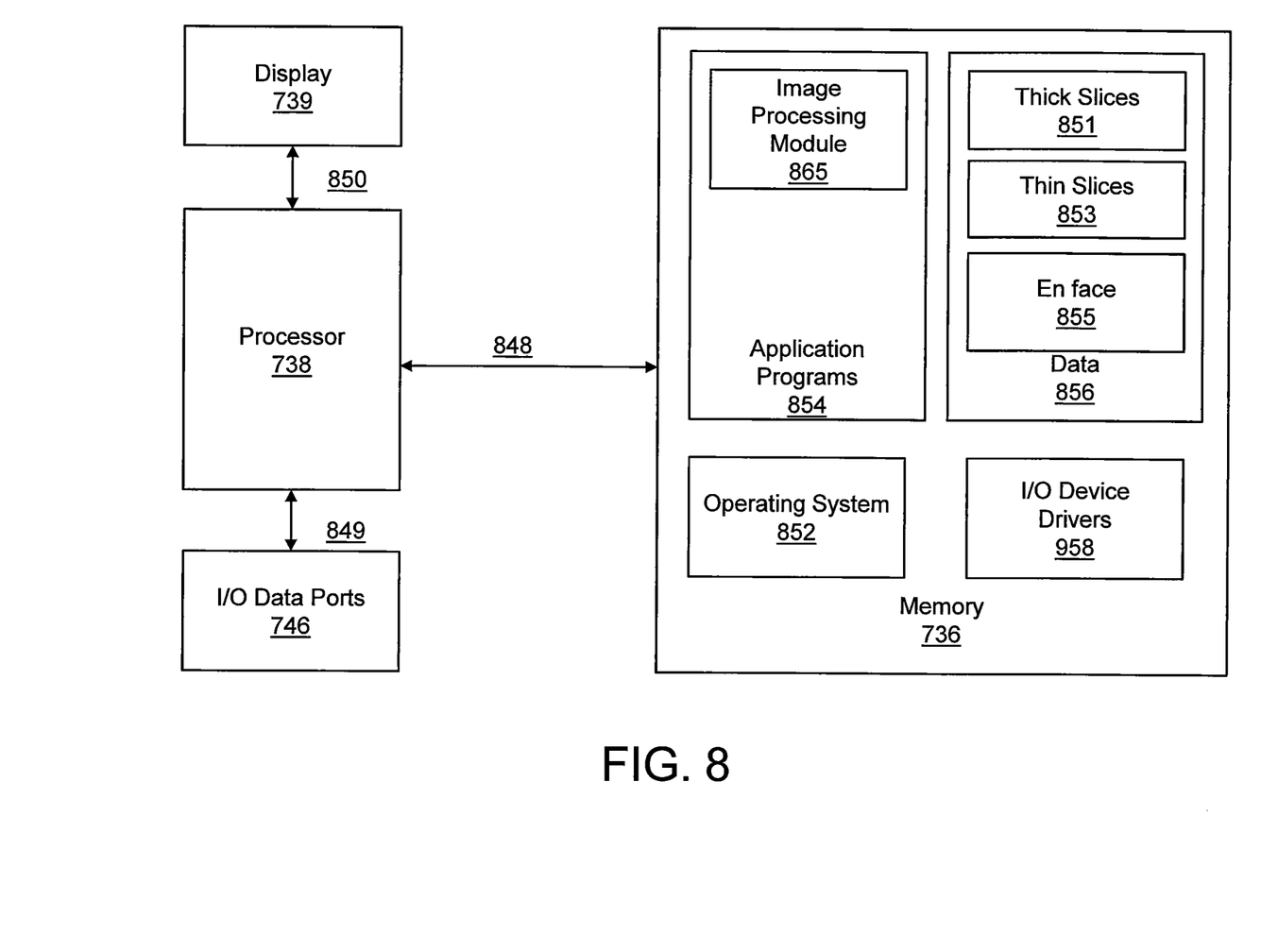
FIG. 8 is a more detailed block diagram of a data processing system of FIG. 7 in accordance with some embodiments of the present inventive concept.

Referring now to FIG. 8, a more detailed block diagram of a data processing system of FIG. 7 is provided that illustrates systems, methods, and computer program products in accordance with some embodiments of the present inventive concept, which will now be discussed. As illustrated in FIG. 8, the processor 738 communicates with the memory 736 via an address/data bus 848, the I/O data ports 746 via address/data bus 849 and the electronic display 839 via address/data bus 850. The processor 738 can be any commercially available or custom enterprise, application, personal, pervasive and/or embedded microprocessor, microcontroller, digital signal processor or the like. The memory 836 may include any memory device containing the software and data used to implement the functionality of the data processing system 730. The memory 736 can include, but is not limited to, the following types of devices: ROM, PROM, EPROM, EEPROM, flash memory, SRAM, and DRAM.

As further illustrated in FIG. 8, the memory 736 may include several categories of software and data used in the system: an operating system 852; application programs 854; input/output (I/O) device drivers 858; and data 856. As will be appreciated by those of skill in the art, the operating system 852 may be any operating system suitable for use with a data processing system, such as OS/2, AIX or zOS from International Business Machines Corporation, Armonk, N.Y., Windows95, Windows98, Windows2000 or WindowsXP, or Windows CE or Windows 7 from Microsoft Corporation, Redmond, Wash., Palm OS, Symbian OS, Cisco IOS, VxWorks, Unix or Linux. The I/O device drivers 858 typically include software routines assessed through the operating system 852 by the application programs 854 to communicate with devices such as the I/O data port(s) 746 and certain memory 736 components. The application programs 854 are illustrative of the programs that implement the various features of the some embodiments of the present inventive concept and may include at least one application that supports operations according to embodiments of the present inventive concept. Finally, as illustrated, the data 856 may include the thick slices 851, the thin slices 853, en face images 855 and any of the data acquired and stored by the system, which may represent the static and dynamic data used by the application programs 854, the operating system 852, the I/O device drivers 858, and other software programs that may reside in the memory 736.

As further illustrated in FIG. 8, according to some embodiments of the present inventive concept, the application programs 854 include an image processing module 865. While the present inventive concept is illustrated with reference to image processing module 965 being an application program FIG. 8, as will be appreciated by those of skill in the art, other configurations fall within the scope of the present inventive concept. For example, rather than being an application program 854, these circuits and modules may also be incorporated into the operating system 852 or other such logical division of the data processing system. Furthermore, while the image processing module 865 is illustrated in a single system, as will be appreciated by those of skill in the art, such functionality may be distributed across one or more systems. Thus, the present inventive concept should not be construed as limited to the configuration illustrated in FIG. 8, but may be provided by other arrangements and/or divisions of functions between data processing systems. For example, although FIG. 8 is illustrated as having various circuits, one or more of these circuits may be combined without departing from the scope of the present inventive concept.

It will be understood that the image processing module 865 may be used to implement various portions of the present inventive concept capable of being performed by a data processing system. For example, the image processing module 865 may be used to process and assess the images produced by the OCT system according to some embodiments of the present inventive concept.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A method of deriving and displaying an image, the method comprising:
    deriving a first boundary surface from a volumetric image using a process of layer segmentation;
    deriving a second boundary surface, different and spaced apart from the first boundary surface, of the volumetric image using the process of layer segmentation, the first and second boundary surfaces defining a slice of the volumetric image therebetween;
    deriving a third boundary surface between the first and second boundary surfaces, wherein the third boundary surface is axially displaced from the first boundary surface in a first proportion to a local axial distance between the first and second boundary surfaces;
    deriving a fourth boundary surface between the third and second boundary surfaces, wherein the fourth boundary surface is axially displaced from the second boundary surface in a second proportion to the local axial distance between the first and second boundary surfaces;
    deriving at least one intermediate thin section between the third and fourth boundary surfaces, the thin section having a thickness that is less than a thickness of the slice of the volumetric image defined by the first and second boundary surfaces and excluding data between the first and third boundary surfaces and data between the fourth and second boundary surfaces;
    deriving a two dimensional en face surface projection from the data within the intermediate thin section; and
    displaying the en face surface projection,
    wherein at least one of the deriving of the first boundary, the deriving of the second boundary and the deriving of the at least one intermediate thin section is performed by at least one processor.

2. The method of claim 1, wherein the volumetric image is acquired using optical coherence tomography (OCT).

3. The method of claim 2, wherein the volumetric image is acquired using Fourier domain OCT (FDOCT).

4. A system for deriving and displaying an image, the system comprising:
    an imaging system for acquiring a volumetric image;
    an image processing module coupled to the imaging system, the image processing module being configured to:
    derive a first boundary surface from a volumetric image using a process of layer segmentation;
    derive a second boundary surface, different and spaced apart from the first boundary surface, of the volumetric image using a process of layer segmentation, the first and second boundary surfaces defining a slice of the volumetric image therebetween;
    derive a third boundary surface between the first and second boundary surfaces, wherein the third boundary surface is axially displaced from the first boundary surface in a first proportion to a local axial distance between the first and second boundary surfaces;
    derive a fourth boundary surface between the third and second boundary surfaces, wherein the fourth boundary surface is axially displaced from the second boundary surface in a second proportion to the local axial distance between the first and second boundary surfaces;
    derive at least one intermediate thin section between the third and fourth boundary surfaces, the thin section having a thickness that is less than a thickness of the slice of the volumetric image defined by the first and second boundary surfaces and excluding data between the first and third boundary surfaces and data between the fourth and second boundary surfaces;

derive a two dimensional en face surface projection from the data within the intermediate thin section; and display the en face surface projection.

5. The system of claim 4, where the image acquisition system comprises an optical coherence tomography (OCT) system.

6. The system of claim 5, wherein the OCT system comprises a Fourier domain OCT (FDOCT) system.

7. A computer program product for deriving and displaying an image, the computer program product comprising:

a non-transitory computer readable storage medium having computer readable program code embodied in the medium, the computer readable program code comprising:

computer readable program code to derive a first boundary surface from a volumetric image using a process of layer segmentation;

computer readable program code configured to derive a second boundary surface, different and spaced apart from the first boundary surface, of the volumetric image using a process of layer segmentation, the first and second boundary surfaces defining a slice of the volumetric image therebetween;

computer readable program code configured to derive a third boundary surface between the first and second boundary surfaces, wherein the third boundary surface is axially displaced from the first boundary surface in a first proportion to a local axial distance between the first and second boundary surfaces;

computer readable program code configured to derive a fourth boundary surface between the third and second boundary surfaces, wherein the fourth boundary surface is axially displaced from the second boundary surface in a second proportion to the local axial distance between the first and second boundary surfaces;

computer readable program, code configured to derive at least one intermediate thin section between the third and fourth boundary surfaces, the thin section having a thickness that is less than a thickness of the slice of the volumetric image defined by the first and second boundary surfaces and excluding data between the first and third boundary surfaces and data between the fourth and second boundary surfaces;

computer readable program code to derive a two dimensional en face surface projection from the data within the intermediate thin section; and computer readable program code to display the en face surface projection.

8. The computer program product of claim 7, wherein the volumetric image is acquired using optical coherence tomography (OCT).

9. The computer program product of claim 8, wherein the volumetric image is acquired using Fourier domain OCT (FDOCT).

* * * * *